(12) United States Patent
Hardaway

(10) Patent No.: US 8,050,941 B2
(45) Date of Patent: Nov. 1, 2011

(54) SYSTEM AND METHOD FOR DISPERSING MEDICATIONS USING A SINGLE POINT PURCHASE

(75) Inventor: Jason Michael Hardaway, Portland, OR (US)

(73) Assignee: Wellpartner Incorporated, Portland, OR (US)

( * ) Notice: Subject to any disclaimer, the term of this patent is extended or adjusted under 35 U.S.C. 154(b) by 693 days.

(21) Appl. No.: 12/117,467

(22) Filed: May 8, 2008

(65) Prior Publication Data

US 2009/0281824 A1 Nov. 12, 2009

(51) Int. Cl.
*G06Q 50/00* (2006.01)
(52) U.S. Cl. .............................................. 705/2; 705/28
(58) Field of Classification Search .................. 705/2–3, 705/28
See application file for complete search history.

(56) References Cited

U.S. PATENT DOCUMENTS

| | | | |
|---|---|---|---|
| 6,055,507 A * | 4/2000 | Cunningham | ..................... 705/3 |
| 7,640,170 B1 | 12/2009 | Gourley | |
| 2001/0037216 A1 | 11/2001 | Oscar et al. | |
| 2002/0002495 A1 | 1/2002 | Ullman | |
| 2002/0069088 A1 | 6/2002 | Berg | |
| 2006/0184391 A1 | 8/2006 | Barre et al. | |
| 2007/0233517 A1 | 10/2007 | Dayal | |
| 2007/0233522 A1 | 10/2007 | Dayal | |
| 2008/0288281 A1 * | 11/2008 | Shell et al. | ........................ 705/2 |
| 2009/0281823 A1 | 11/2009 | Hardaway | |
| 2011/0054935 A1 | 3/2011 | Hardaway | |

OTHER PUBLICATIONS

Non-final Office Action for U.S. Appl. No. 12/145,960 filed Jun. 25, 2008, mailed from the USPTO on Apr. 1, 2011, 25 pgs.
Non-final Office Action for U.S. Appl. No. 12/117,447 filed May 8, 2008, mailed from the USPTO on Jun. 22, 2010, 10 pgs.
Final Office Action for U.S. Appl. No. 12/117,447 filed May 8, 2008, mailed from the USPTO on Jan. 5, 2011, 12 pgs.

* cited by examiner

*Primary Examiner* — Gerald J. O'Connor
*Assistant Examiner* — Minnah Seoh
(74) *Attorney, Agent, or Firm* — John R. Thompson; Stoel Rives LLP

(57) ABSTRACT

A computer system and method manages the dispersal and replenishment of medications. Participating health care providers are associated with a code that corresponds to medication units dispersed by a pharmacy. The amount of medication units corresponding to the code and dispersed to patients of the health care providers is tracked. When the amount of dispersed medication units reaches a replenishment threshold, replacement medication units are ordered.

18 Claims, 3 Drawing Sheets

SYSTEM AND METHOD FOR DISPERSING MEDICATIONS USING A SINGLE POINT PURCHASE

TECHNICAL FIELD

This disclosure relates generally to techniques for managing the dispersal and replenishment of pharmaceutical inventories.

BRIEF DESCRIPTION OF THE DRAWINGS

Non-limiting and non-exhaustive embodiments of the disclosure are described, including various embodiments of the disclosure with reference to the figures, in which.

DETAILED DESCRIPTION OF PREFERRED EMBODIMENTS

Figure 1:
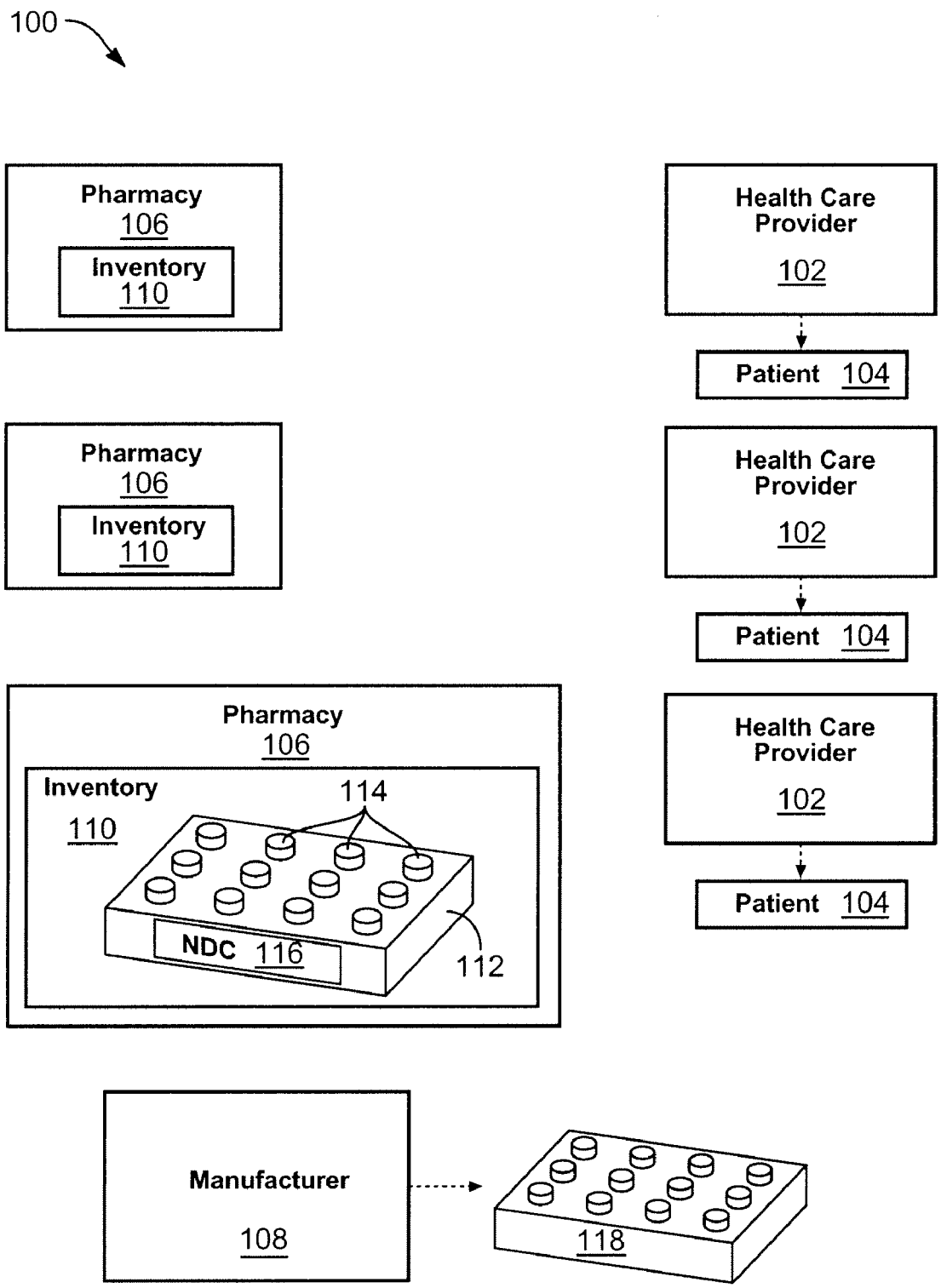
FIG. 1 is a block diagram of a system for distributing prescribed medications.

The described features, structures, or characteristics may be combined in any suitable manner in one or more embodiments. Those skilled in the art will recognize that the invention can be practiced without one or more of the specific details, or with other methods, components, materials, etc. In other instances, well-known structures, materials, or operations are not shown in detail to avoid obscuring aspects of the invention.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawing or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable storage medium having stored thereon instructions that may be used to program a computer (or other electronic device) to perform processes described herein. The machine-readable storage medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

Suitable networks for configuration and/or use as described here include one or more local area networks, wide area networks, metropolitan area networks, and/or "Internet" or IP networks, such as the World Wide Web, a private Internet, a secure Internet, a value-added network, a virtual private network, an extranet, an intranet, or even standalone machines which communicate with other machines by physical transport of media (a so-called "sneakernet"). In particular, a suitable network may be formed from parts or entireties of two or more other networks, including networks using disparate hardware and network communication technologies.

One suitable network includes a server and several clients; other suitable networks may contain other combinations of servers, clients, and/or peer-to-peer nodes, and a given computer may function both as a client and as a server. Each network includes at least two computers, such as the server and/or clients. A computer may be a workstation, laptop computer, disconnectable mobile computer, server, mainframe, cluster, so-called "network computer" or "thin client", personal digital assistant or other hand-held computing device, "smart" consumer electronics device or appliance, or a combination thereof.

The network may include communications or networking software, such as the software available from Novell, Microsoft, Artisoft, and other vendors, and may operate using TCP/IP, SPX, IPX, and other protocols over twisted pair, coaxial, or optical fiber cables, telephone lines, satellites, microwave relays, modulated AC power lines, physical media transfer, and/or other data transmission "wires" known to those of skill in the art. The network may encompass smaller networks and/or be connectable to other networks through a gateway or similar mechanism.

Each computer includes at least a processor and a memory; computers may also include various input devices and/or output devices. The processor may include a general purpose device, such as a 80.times.86, Pentium (mark of Intel), 680.times.0, or other "off-the-shelf" microprocessor. The processor may include a special purpose processing device, such as an ASIC, PAL, PLA, PLD, Field Programmable Gate Array, or other customized or programmable device. The memory may include static RAM, dynamic RAM, flash memory, ROM, CD-ROM, disk, tape, magnetic, optical, or other computer storage medium. The input device(s) may include a keyboard, mouse, touch screen, light pen, tablet, microphone, sensor, or other hardware with accompanying firmware and/or software. The output device(s) may include a monitor or other display, printer, speech or text synthesizer, switch, signal line, or other hardware with accompanying firmware and/or software.

The computers may be capable of using a floppy drive, tape drive, optical drive, magneto-optical drive, or other means to read a storage medium. A suitable storage medium includes a magnetic, optical, or other computer-readable storage device having a specific physical configuration. Suitable storage devices include floppy disks, hard disks, tape, CD-ROMs, DVDs, PROMs, random access memory, flash memory, and other computer system storage devices. The physical configuration represents data and instructions which cause the computer system to operate in a specific and predefined manner as described herein.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent art(s).

Several aspects of the embodiments described will be illustrated as software modules or components. As used herein, a software module or component may include any type of computer instruction or computer executable code located within a memory device. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Much of the infrastructure that can be used according to the present invention is already available, such as: general purpose computers; computer programming tools and techniques; computer networks and networking technologies; digital storage media; authentication, access control, and other security tools and techniques provided by public keys, encryption, firewalls, and/or other means.

Referring to FIG. 1, a block diagram of participants in a system 100 for dispersing and replenishing medications is shown. A plurality of health care providers 102 provide health care services to patients 104. Medications are dispensed to the patients 104 through the use of one or more pharmacies 106 under the supervision of a health care provider 102. Depending on the arrangement, the pharmacy 106 may provide medications to the health care provider 102 or may provide medications directly to the patients 104. The pharmacy 106 replenishes medication inventories from pharmaceutical manufacturers 108. As can be appreciated, a wide variety of programs may be involved in providing health care services and dispersing medications, and these programs often impact pricing.

One federal program is the 340B program, also known as the section 602 or "PHS" pricing, is a federally administered program that allows certain qualified health care providers (covered providers) 102 within the health care safety-net to purchase outpatient medications from manufacturers 108 at or below a defined discount price. It is important to note that the 340B program is not a governmental purchasing program but is a discount programmed administered by the federal government. Pharmaceutical manufacturers 108 are required to sell covered medications to certain covered providers 102 at or below a statutorily defined "ceiling price" as a condition for Medicaid participation. The 340B price is the ceiling price, meaning it is the most that covered providers 102 can be charged for medications purchased directly from manufacturers 108. In compliance with statutes, the ceiling price may be derived from Medicaid pricing. Covered providers 102 are allowed, and even encouraged, to negotiate sub-ceiling prices either with manufacturers 108. In addition to providing a pricing structure for safety-net providers, the 304B program establishes eligibility requirements for covered providers 102. Thus, the covered providers 102 are able to realize substantial cost reductions on medications used for patients 104 in an outpatient setting. Covered medications may include any medication reimbursed by Medicaid, including prescription or over-the-counter medications.

Eligibility for health care providers 102 is established by federal statute, and eligible providers 102 include recipients of certain federal grants. Eligibility for participation in a 340B program is determined by providers status, specifically by receiving one of several grants or by being a certain type of disproportionate share hospital or federally qualified health center (FQHC) or look-alike. Eligible health care providers 102 include core safety-net providers and a number of health facilities. Various FQHCs may be eligible health care providers 102, such as consolidated health centers, migrant health centers, health care for the homeless, school-based health centers, public housing health centers, PL 93-638 tribal health centers, urban Indian health centers, and qualified community health clinics. Other eligible entities may also include FQHC look-alikes, native Hawaiian health centers, Ryan White Care Act Grantees, Title X Family Planning, black lung clinics, comprehensive hemophilia diagnostic treatment centers, state or locally funded centers treating sexually transmitted diseases or tuberculosis, certain disproportionate share hospitals, and other safety-net organizations.

A patient who receives medication through a 340B program must be a patient 104 of a covered provider 102. This requirement prevents against the risk of diversion of 340B program products to non-qualified patients. The 340B program prohibits all forms of medication resale or diversion. Diversion is the distribution of 340B medications to non-340B eligible patients, either intentionally or unintentionally. The covered provider 102 may not resell or transfer the drug to a person who is not a patient of the provider 102.

The 340B program further prohibits "double-dipping." Covered providers 102 cannot request 340B prices for the same medication for which Medicaid will request a rebate. With this prohibition, a covered provider 102 can receive a discount through the 340B program, or Medicaid can receive a discount via rebate. However, both may not occur for the same medication.

Covered providers 102 may provide 340B pharmacy access for their patients through one of three methods. A first method is a clinic dispensary which is an on-site dispensing cabinet utilizing a small inventory of basic medications. A second method is a full-service, in-house pharmacy created and operated by the provider 102 on its premises. A third method is a contracted pharmacy which is an external pharmacy under contract with the covered provider 102 to provide pharmacy services and medications to the provider 102 and/or provider's patients. Since the 340B program is a provider-specific medication discount program, the provider is the only organization that can legally purchase 340B medications. Therefore, a contracted pharmacy must operate under a "bill-to/ship-to" arrangement, where medications are shipped by the drug wholesaler directly to the pharmacy, and the bill for the medications is sent to the health care provider 102.

When dispensing medications to patients, including patients 104 of the health care providers 102, a pharmacy 106 may operate using a "replenishment model." The replenishment model is used in the 340B program and, in one implementation, enables a contracted pharmacy 106 to manage their 340B inventory virtually while receiving 340B replacement product on a replenishment basis. In one implementation, the replenishment model provides a form of inventory control. The replenishment model allows a contracted pharmacy 106 to dispense medication to 340B covered patients 104 from its own inventory 110, and then have that inventory 110 replenished by the covered provider 102. In effect, the contracted pharmacy 106 "loans" the covered provider 102 the medication, and the covered provider 102 then orders replacement inventory. The advantage of this approach is that it reduces the likelihood of medication diversion, as there is no specific 340B inventory sitting on the contract pharmacy's shelves. Another method of inventory control involves maintaining a separate physical inventory. However, the replenishment model is very effective in preventing diversion and double-dipping while also providing an option for reduced costs.

In an inventory 110, containers 112 include a quantity of medication units 114. The medication units 114 are discrete units and may be dispensed to patients 104 and/or the health care provider 102. A container 112 may have a corresponding national drug code (NDC) 116, or other identifying code, that identifies the type of medication and the number of medication units 114. Typically, the number of medication units in a NDC 116 remains unchanged even after one or more replenishments. Under the replenishment model, inventory replenishment may include determining the quantity of medication units 114 corresponding to and dispensed from a particular NDC 116.

A pharmacy 106 orders a replacement container 118 from a manufacturer 108 when the number of dispensed medication units 114 for the original container 112 and the NDC 116 meets or exceeds a replenishment threshold. The replenishment threshold is typically the number of medication units 114 in both the original and the replacement containers 112, 118 and that number is also reflected in the corresponding NDC 116.

A difficulty arises when, after a certain time period, the number of dispensed medication units does not equal the number of medication units 114 in that particular NDC 116. As can be expected, after a certain time interval a pharmacy 106 desires to replenish its inventory 110 and have payment for dispersed medication units. A pharmacy 106 may desire this replenishment even though a replenishment threshold has not yet been met for a container 112. Thus, after a time period, a pharmacy 106 may have a policy of automatically replenishing a NDC 116. This automatic replenishment after a certain time period is referred to herein as "trueing-up." The time period may be any number of days, weeks, or months that a pharmacy 106 sets as its policy.

When a true-up occurs, a health care provider 102 is charged the replacement cost of the dispensed medication units at the pharmacy's acquisition price. The acquisition price may be significantly greater than a price under the 340B program. This can lead to significantly increased costs for the health care provider 102. A further point of complexity is that, if the health care provider 102 has a number of contract pharmacies 106, then the risk of "true-ups" occurring increases proportional to the number of additional pharmacies 106 participating. As can be appreciated, with multiple pharmacies 106, there is an increased risk of partially depleted containers occurring after a predetermined time period.

Figure 2:
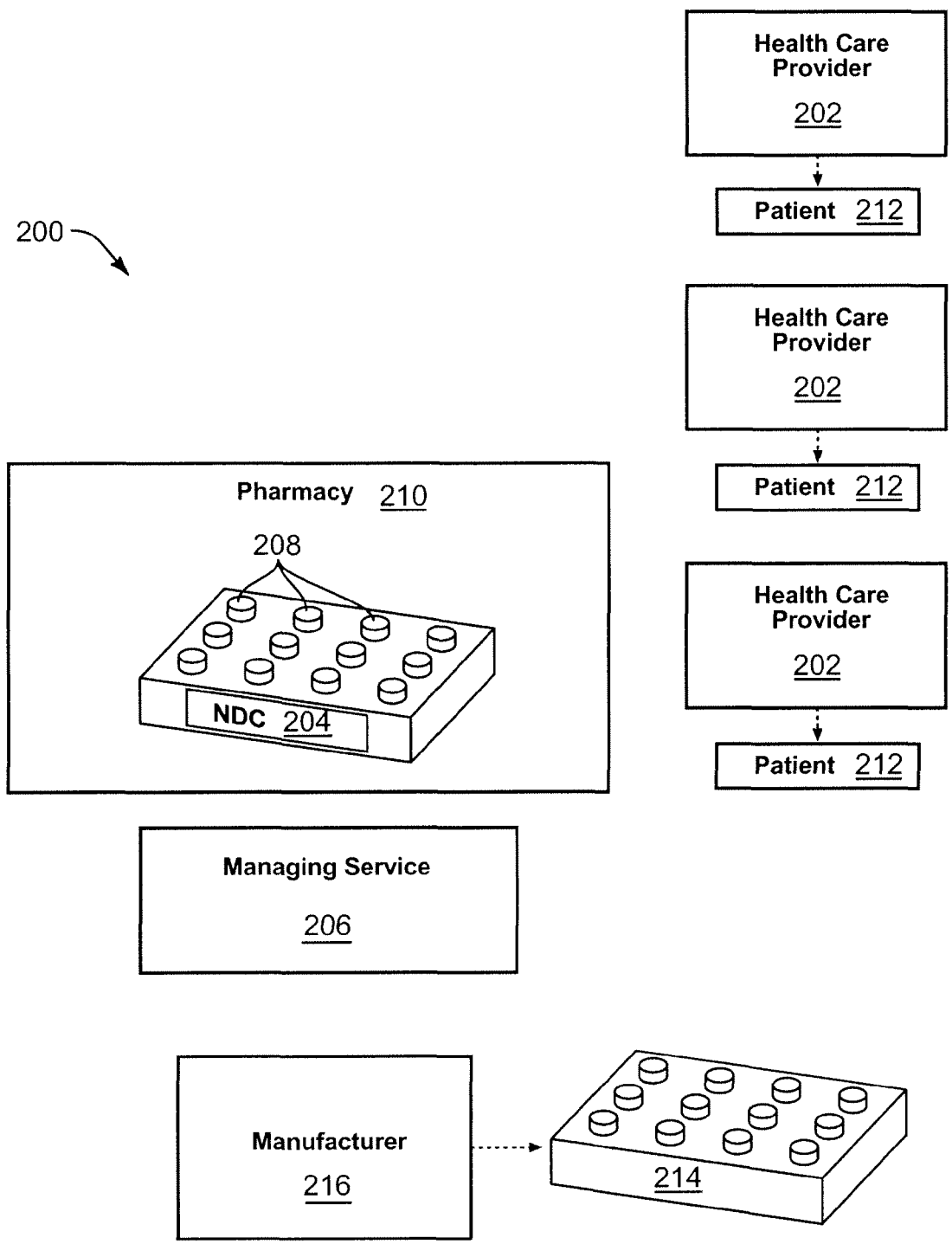
FIG. 2 is a block diagram of an alternative system for distributing prescribed medications.

Referring to FIG. 2, a block diagram of a system 200 for dispersing medications through a single point purchase is shown. The system 200 minimizes the risk of "true-ups" by using associating a plurality of health care providers 202 with a NDC 204. The provider's association with one another may be through any number of relationships, such as contractual or ownership relationships. For example, the providers 202 may have contractual agreements with one another or be members of the same company, franchise, chain, or be affiliated in some other manner. The association may be simply based on the economic advantages in participating in the system 200.

A managing service 206 is in communication with each health care provider 202 and tracks the NDC 204 and corresponding medication units 208. The managing service 206 provides the oversight and resources to ensure that the 340B program is successfully implemented and administered on behalf of the covered health care providers 202. The NDC 204 and medication units 208 may be physically stored at a pharmacy 210. As such, the heath care providers 202 may require that their prescriptions be filled at a particular pharmacy 210. A patient may also have their prescription filled at another pharmacy which provides an effective loan of a medication unit and then seeks reimbursement from the participating pharmacy 210. Alternatively, the NDC 204 may be physically stored at one of the health care provider facilities. This is advantageous where a health care provider 202 maintains an in-house pharmacy.

The managing service 206 tracks filled and dispensed prescriptions relating to the NDC 204 for all of the health care providers 202. By filling prescriptions, medication units 208 are dispensed to patients 212 of health care providers 202. The managing service 206 determines when the combined number of all of the medication units 208 for all of the prescriptions reaches the replenishment threshold of a particular NDC 204. When the replenishment threshold is reached, the managing service 206 initiates an order for a replacement container 214. This may require that the pharmacy 210 place the order for the replacement container 214 from a pharmaceutical manufacturer 216.

The replacement container 214 is credited to the pharmacy 210 and all participating health care providers 202 have dispersal rights to receive medication units 208 from the NDC 204. Thus, the health care providers 202 combine their dispensing from the NDC 204 to minimize the opportunity for a true-up situation.

Figure 3:
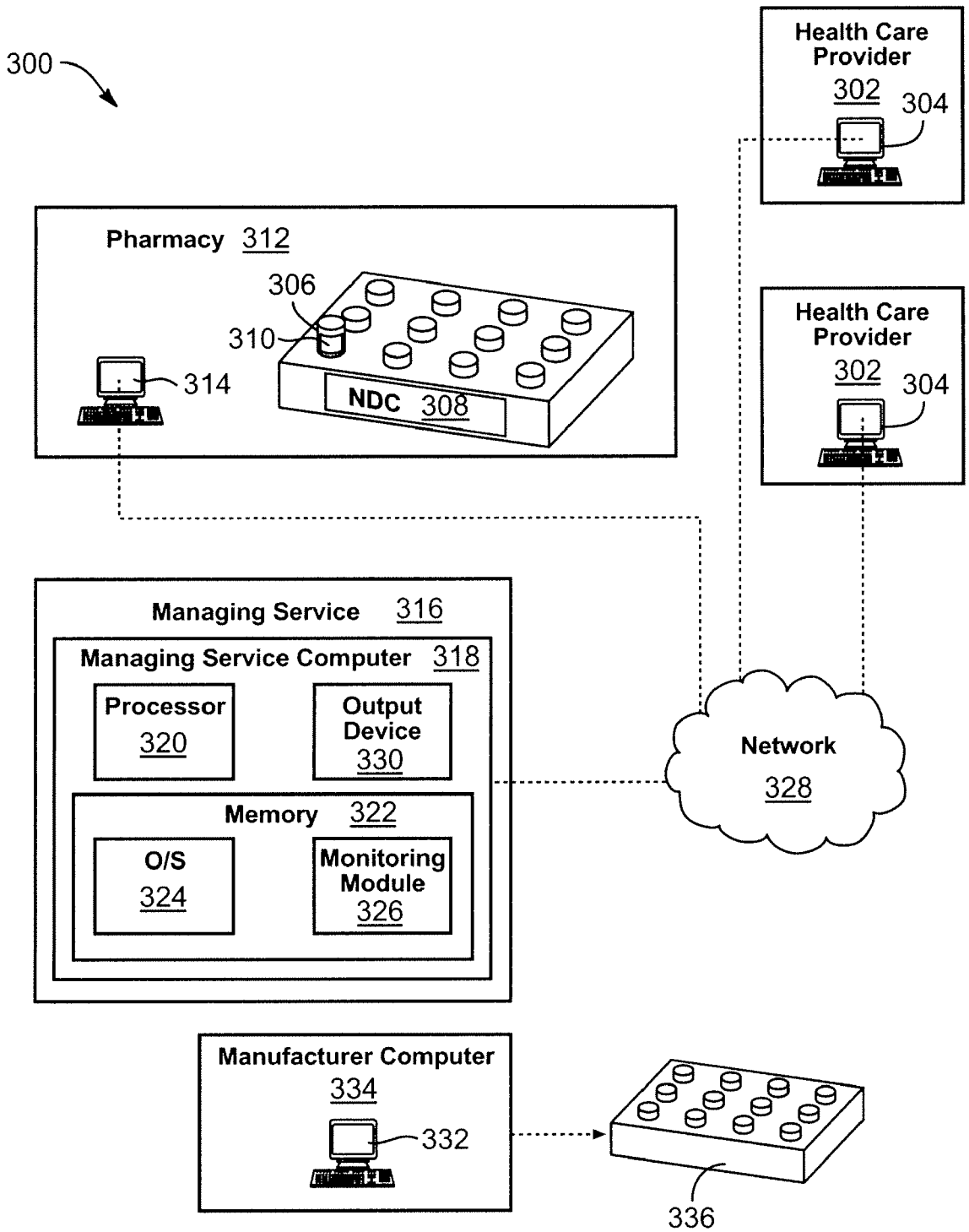
FIG. 3 is a block diagram of a system for distributing prescribed medications.

Referring to FIG. 3, a system 300 for tracking medication dispersals using a single point purchase is shown. Each health care provider 302 may include one or more computers 304 to record a prescription of a medication unit 306 corresponding to a NDC 308. Input to a computer 304 to record and track a medication unit dispersal may be performed in a variety of ways including manual entry, such as by typing an identifier through use of a keyboard, or optical scanning technology. When a prescription is generated, a record may also be automatically generated to track the prescription issuance.

In one embodiment, bar code technology may be used to track prescriptions and medication units 306 throughout the fulfillment process. Each medication unit 306 may include a corresponding bar code 310 which is disposed on the unit 306. The bar code 310 may include information as to the type of medication, the corresponding NDC 308, the amount of medication, the cost, etc. An optical scanner or other device used for scanning may be in electrical communication with the computer 304 through any one of a number of conventional networks. A prescription may also include a bar code which includes information on the type of medication, the prescription refills, the health care provider 302, and other relevant information.

In order to fill a prescription corresponding to the NDC 308, the prescription may be taken to a pharmacy 312 that operates as a single point of purchase. The pharmacy 312 may physically store and dispense all of the medication units 306 corresponding to the NDC 308. Dispersal of the medication units from the NDC 308 may be limited only to prescriptions of participating health care providers 302. When a prescription is filled, the prescription may be scanned and prescription information may be stored in a pharmacy computer 314. Similarly, the medication unit 306 may be scanned, and corresponding medication unit information may be stored in the pharmacy computer 314. The NDC 308 may also be scanned and the code entered into the pharmacy computer 314. Scanning the NDC 308 may involve reading the code on a storage container. The pharmacy 312 may also include a database (not shown) for storing prescription, medication unit information, and the NDC 308.

A managing service 316 may include a managing service computer 318 comprising a processor 320 and a memory 322 including any of the memory embodiments discussed above. The memory 322 may include an operating system 324 and a monitoring module 326 to track the dispersal of medication units 306 and determine when the dispersal reaches a replenishment threshold.

The managing service computer 318 may be in electrical communication with the health care provider computers 304 and the pharmacy computer 314 through a network 328. The managing service computer 318 associates the participating health care providers 302 with the NDC 308 that corresponds to medication units 306 being dispensed in response to prescriptions. The monitoring module 326 tracks the amount of dispensed medication units 306 and determines when the replenishment threshold is reached.

In one embodiment, upon reaching the replenishment threshold, the managing service computer 318 may notify a user through an output device 330. The output device 330 may include a monitor or display running a suitable graphical user interface to thereby notify a user. Notification may also be performed through a variety of other techniques including email, updating a record in a database, hardcopy print-out, updating a spreadsheet, and the like.

The managing service computer 318 may be in electrical communication through the network 328, or another network, with a manufacturer computer 332 of a manufacturer 334. When a replenishment threshold corresponding to a NDC 308 is reached, the managing service computer 318 may notify the manufacturer computer 332 and place an order for a replacement container 336. The replacement container 336 typically comprises the same number of medication units. In this manner, a NDC 308 is replaced expeditiously, and the risk of a true-up situation is minimized.

The managing service computer 318 may notify a health care provider computer 304 of when a prescription is received at the participating pharmacy 312, when the prescription is filled, and the medication unit 306 that is dispensed. A health care provider 302 is thereby informed of the status of prescriptions provided to its patients. If desired, the health care provider 302 may also be informed as to the replenishment of a NDC 308. As disclosed herein, the system 300 is able to ensure compliance with the 340B program and avoid true-up situations.

The managing service computer 318 may further maintain an account corresponding to the NDC 308 and the health care providers 302. The account may include information regarding the dispersal of the medication units 306, a charge associated with the dispersal of each medication unit 306, orders for replacement containers 336 corresponding to the NDC 308, and the charge associated with the dispersal of each replacement container 336. The managing service computer 318 may determine each health care provider's share of cost for the replacement container 336. As can be appreciated, calculating share of cost may be determined in a variety of ways but typically is proportional to the number of medication units 306 prescribed by each health care provider 302. The managing service computer 318 may further generate an invoice for each health care provider 302 to convey the share of cost. The invoice may be communicated to each health care provider 302 over the network 328.

As disclosed herein, associated health care providers contract with a single pharmacy to collectively fill prescriptions corresponding to a NDC. As can be appreciated, multiple NDCs may be replenished for associated health care providers. The overall costs associated with a "true-up" situation may be avoided, and the benefits of participating in a 340B program may be more fully realized. After health care providers collectively reach replenishment threshold for a NDC, a managing service orders a replacement container for the corresponding NDC.

It will be obvious to those having skill in the art that many changes may be made to the details of the above-described embodiments without departing from the underlying principles of the disclosure.

What is claimed is:

1. A computer system to manage the replenishment of medications dispensed to covered patients of a plurality of unaffiliated qualified health care providers by an independent contract pharmacy common to the unaffiliated qualified health care providers, wherein the unaffiliated qualified health care providers are entitled to purchase discounted medication for the covered patients through respective statutory programs, and wherein the contract pharmacy is strictly prohibited from purchasing discounted medication under the statutory programs, the system comprising:

a processor; and
a memory in electrical communication with the processor, the memory including, a monitoring module to
  receive indications from the independent contract pharmacy of medication units dispensed to the covered patients, wherein the covered patients qualify for discounted medication through a statutory program of a respective qualified health care provider;
  associate the medication units dispensed to the covered patients with a national drug code, the national drug code determining an order quantity of a replacement container of the dispensed medication units that qualifies for a discount under a statutory program of a qualified health care provider;
  allocate each of the medication units dispensed to the covered patients to the independent contract pharmacy and a respective qualified health care provider;
  determine a combined amount of medication units associated with the national drug code dispensed to the covered patients across the plurality of unaffiliated qualified health care providers;
  determine when the combined amount of medication units dispensed by the independent contract pharmacy to the covered patients of the unaffiliated qualified health care providers reaches a replenishment threshold corresponding to the order quantity of the national drug code; and
  upon reaching the replenishment threshold, to replenish the combined amount of medication units of the national drug code to the independent contract pharmacy by,
    providing for purchasing a discounted replacement container of medication units under a statutory program of the unaffiliated qualified health care providers, and
    transferring ownership of the purchased replacement container to the independent contract pharmacy.

2. The system of claim 1, wherein the monitoring module, maintains an account for the plurality of unaffiliated qualified health care providers, the account reflecting the dispensing of the medication units to covered patients, a charge associated with the dispensing of each medication unit, orders for replacement containers corresponding to the national drug code of the dispensed medication units, and the charge associated with each replacement container.

3. The system of claim 1, wherein the monitoring module, determines each unaffiliated qualified health care provider's share of a cost of the replacement container of medication units according to an amount of medication units dispensed to the covered patients of each unaffiliated qualified health care provider.

4. The system of claim 1, wherein the monitoring module, generates an invoice for each unaffiliated qualified health care provider, each invoice reflecting a corresponding share of cost of the replacement container.

5. The system of claim 1, further comprising an output device in electrical communication with the processor and wherein the monitoring module,
provides notification to a user upon reaching the replenishment threshold.

6. The system of claim 1, wherein the monitoring module receives the indications of medication units dispensed to the covered patients of the health care providers from the independent contract pharmacy over a network.

7. A non-transitory computer-readable storage medium, having stored thereon instructions to cause a computing device for performing a method for replenishing medication dispensed to covered patients of a plurality of unaffiliated qualified health care providers by an independent contract pharmacy, wherein the unaffiliated qualified health care providers are entitled to purchase discounted medication for the covered patients through respective statutory programs, and wherein the independent contract pharmacy is strictly prohibited from purchasing discounted medication under the statutory programs, the method comprising:
receiving indications from the independent contract pharmacy of medication units dispensed to the covered patients, wherein the covered patients qualify for discounted medication through a statutory program of a respective qualified health care provider;
associating the medication units dispensed to the covered patients with a national drug code, the national drug code determining an order quantity of a replacement container of the dispensed medication units that qualifies for a discount under a statutory program of a qualified health care provider;
allocating each of the medication units dispensed to the covered patients to the independent contract pharmacy and a respective qualified health care provider;
determining a combined amount of medication units associated with the national drug code dispensed to the covered patients across the plurality of unaffiliated qualified health care providers;
determining when the combined amount of medication units dispensed by the independent contract pharmacy to the covered patients of the unaffiliated qualified health care providers reaches a replenishment threshold corresponding to the order quantity of the national drug code; and
upon reaching the replenishment threshold, replenishing the combined amount of medication units of the national drug code to the independent contract pharmacy by,
providing for purchasing a discounted replacement container of medication units under a statutory program of the unaffiliated qualified health care providers, and transferring ownership of the purchased replacement container to the independent contract pharmacy.

8. The computer readable storage medium of claim 7, wherein the method further comprises:
maintaining an account for the plurality of unaffiliated qualified health care providers, the account reflecting the dispensing of the medication units, a charge associated with the dispensing of each medication unit, orders for replacement containers corresponding to the national drug code of the dispensed medication units, and the charge associated with each replacement container.

9. The computer readable storage medium of claim 7, wherein the method further comprises:
determining each unaffiliated qualified health care provider's share of a cost of the replacement container of medication units according to an amount of medication units dispensed to the covered patients of each unaffiliated qualified health care provider.

10. The computer readable storage medium of claim 7, wherein the method further comprises:
generating an invoice for each unaffiliated qualified health care provider, each invoice reflecting a corresponding share of cost of the replacement container.

11. The computer readable storage medium of claim 7, wherein the method further comprises notifying a user upon reaching the replenishment threshold.

12. The computer readable storage medium of claim 7, the method further comprising receiving the indications of medication units dispensed to the covered patients from the independent contract pharmacy over a network.

13. A computer-implemented method for replenishing medication dispensed to covered patients of a plurality of unaffiliated qualified health care providers by an independent contract pharmacy, wherein the unaffiliated qualified health care providers are entitled to purchase discounted medication for the covered patients through respective statutory programs, and wherein the independent contract pharmacy is strictly prohibited from purchasing discounted medication under the statutory programs, the method comprising:
receiving indications from the independent contract pharmacy of medication units dispensed to the covered patients, wherein the covered patients qualify for discounted medication through a statutory program of a respective unaffiliated qualified health care provider;
associating the medication units dispensed to the covered patients with a national drug code, the national drug code determining an order quantity of a replacement container of the dispensed medication units that qualifies for a discount under a statutory program of an unaffiliated qualified health care provider;
allocating each of the medication units dispensed to the covered patients to the independent contract pharmacy and a respective qualified health care provider;
determining a combined amount of medication units associated with the national drug code dispensed to the covered patients across the plurality of unaffiliated qualified health care providers;
determining when the combined amount of medication units dispensed by the independent contract pharmacy to the covered patients of the unaffiliated qualified health care providers reaches a replenishment threshold corresponding to the order quantity of the national drug code and allocating dispensed medication units by unaffiliated qualified health care providers; and
upon reaching the replenishment threshold, replenishing the combined amount of medication units of the national drug code to the independent contract pharmacy by, providing for purchasing a discounted replacement container of medication units under a statutory program of the unaffiliated qualified health care providers, and transferring ownership of the purchased replacement container to the independent contract pharmacy.

14. The method of claim 13, further comprising:
maintaining an account for the plurality of unaffiliated qualified health care providers, the account reflecting the dispensing of the medication units, a charge associated with the dispensing of each medication unit, orders for replacement containers corresponding to the national drug code of the dispensed medication units, and the charge associated with each replacement container.

15. The method of claim 13, further comprising:
determining each unaffiliated qualified health care provider's share of a cost of the replacement container of medication units according to an amount of medication units dispensed to the covered patients of each unaffiliated qualified health care provider.

16. The method of claim 13, further comprising:
generating an invoice for each unaffiliated qualified health care provider, each invoice reflecting a corresponding share of cost of the replacement container.

17. The method of claim 13, further comprising notifying a user upon reaching the replenishment threshold.

18. The method of claim 13, further comprising receiving the indications of medication units dispensed to the covered patients from the independent contract pharmacy over a network.

\* \* \* \* \*